United States Patent [19]

Petersen et al.

[11] Patent Number: 4,803,155

[45] Date of Patent: Feb. 7, 1989

[54] **MONOCLONAL ANTIBODIES TO *SCLEROTINIA HOMOEOCARPA***

[75] Inventors: Frank P. Petersen, Beverly; Adrianna M. Maybroda, Haddonfield; Sally A. Miller, Pennsauken, all of N.J.

[73] Assignee: Agri-Diagnostics Associates, Cinnaminson, N.J.

[21] Appl. No.: 834,198

[22] Filed: Feb. 27, 1986

[51] Int. Cl.$^4$ .................. G01N 33/53; G01N 33/577; C07K 15/14

[52] U.S. Cl. .......................................... 435/7; 435/34; 435/810; 435/911; 436/518; 436/548; 436/808; 530/387

[58] Field of Search ................. 435/34, 240, 7, 172.2, 435/911, 810; 436/518, 548, 808; 530/387

[56] References Cited

U.S. PATENT DOCUMENTS

| | | | |
|---|---|---|---|
| 3,968,239 | 7/1976 | Ferguson et al. | 514/525 |
| 4,503,143 | 3/1985 | Gerber et al. | 436/510 |

FOREIGN PATENT DOCUMENTS 2138444 10/1984 United Kingdom .

OTHER PUBLICATIONS

Tarig et al, Chemical abstract, vol. 103, abstract No. 34790t, 1985.
Savage et al, Biological abstract, vol. 72, abstract No. 40936, 1981.

*Primary Examiner*—Robert J. Warden
*Assistant Examiner*—Florina Hoffer
*Attorney, Agent, or Firm*—Pennie & Edmonds

[57] ABSTRACT

This invention provides monoclonal antibodies which specifically bind to *Sclerotinia homoeocarpa* the causative agent of dollarspot disease in plants. Hybridoma producing the antibodies as well as materials and kits for carrying out the detection of *Sclerotina homoeocarpa* are also disclosed.

22 Claims, No Drawings

MONOCLONAL ANTIBODIES TO *SCLEROTINIA HOMOEOCARPA*

FIELD OF THE INVENTION

This invention relates to the field of diagnostic plant pathology. More specifically the invention relates to the immunological detection of various taxa of fungi known to be the etiologic agents of a variety of plant diseases.

BACKGROUND OF THE INVENTION

Fungi as a group cause many plant diseases. For purposes of discussion the fungi can be classified as belonging to one of three major taxonomic classes: Basidiomycetes, Phycomycetes, or Ascomycetes.

Basidiomycetes

Members of this class are identified by the presence of a sexual-spore forming structure known as a basidium. Pathogenic forms include smuts, rusts and fleshy species such as mushrooms. Examples include wheat rust, white pine blister, cedar-apple rust, and smuts causing disease in corn, oats, barley, onions and wheat.

Phycomycetes

Members of this class are considered to be more primitive than members of either the Ascomycetes or Basidiomycetes, their distinguishing morphological feature being the absence of mycelial crosswalls. Examples of disease caused by members of the class include the downy mildews of grape and other hosts, root rot and late blight of potato and tomato.

Ascomycetes

Members of this class possess a specialized reproductive structure (an ascus) in which meiosis and sexual spore formation take place. Examples of the more common plant diseases in which Ascomycetes have been identified as the etiologic agent include: powdery mildews on cereals, fruits and many other crops; Dutch elm disease; ergot of grains; peach and plum brown rot; black spot of roses as well as apple scab.

With respect to the present invention, members of the family Sclerotiniaceae, and particularly the genus Sclerotinia, are of particular interest. Several hundred species have been at one time or another assigned to this genus; many of these are important plant pathogens. The family Sclerotiniaceae was erected and discussed at length by Whitzel (*Mycologia*, 37: 648-714, 1945). The taxonomy of the members of the family, and of the genus Sclerotinia, is currently in a state of flux, with many of the members traditionally assigned to the genus being assigned elsewhere (L. Kohn, *Phytopathology*, 69: 881-886, 1979). However, for the purposes of the present invention, any reference to the genus Sclerotinia will be understood by those skilled in the art to mean the genus *Sclerotinia sensu lato*.

As noted above, the members of the family Sclerotiniaceae contain a number of significant pathogens. For example, several species of the genus Monilinia Honey is known to cause brown rot of many stone fruits such as peach, plum and cherry, particularly in Europe. *Sclerotinia sclerotiorum* DBy. causes one of the most widespread diseases of vegetable and field crops attacking clover, sunflower, various bulbous species, lemon, cabbage, tomato and carrot among others. The species *Sclerotinia homoeocarpa* Bennett causes "dollarspot disease", a widespread and highly destructive disease of turfgrasses in Australia, North America and Europe. Again, the taxonomy of the organism is somewhat uncertain, and more than one species may be included in the nominal species. However, for present purposes, the use of the name *Sclerotinia homoeocarpa* is to be understood in its broadest sense, and is intended to include any causative agent of dollarspot diseases.

The above diseases are capable of causing a tremendous economic loss to the growers of afflicted plants each year. Although various chemical treatment methods are known by which these diseases can be controlled to some extent after the presence becomes evident, it is preferable to have a method of detection of the presence of the organism before it has had an opportunity to spread very far. Therefore, a system which allows for very early detection of the presence of the pathogenic fungus would be of tremendous value to the growers and/or keepers of potentially afflicted plants. The present invention enables just such a system to be put into practice by providing monoclonal antibodies which are capable of detecting the presence of Sclerotinia antigens, thus allowing early diagnosis of the disease, and possible prevention of widespread losses to the affected crop.

Hybridoma Monoclonal Antibody Technology

The use of somatic hybrid cell lines as sources of antibody to individual antigens generally dates from the work of Kohler and Milstein (*Nature*, 256: 495-97(1975)). The antibodies produced are quite different than those recovered from antiserum from conventionally immunized animals. Each hybrid cell line synthesizes a homogenous immunoglobulin that represents but one of the myriad of types of antibodies that an animal can synthesize in response to an antigen in vivo. Since each immunoglobulin-producing clone is characterized by the single type of antibody it produces, the term monoclonal antibody has been adopted. The advantages of monoclonal antibodies are numerous; they can be obtained in large supply; the preparation is homogenous with respect to antigen reactivity and remains so over time.

The principle of hybridoma/monoclonal technology is predicated on the observation that when two somatic cells are fused the resultant hybrid displays characteristics of both of the parent cell types. In the case of monoclonal antibody production, the ability to synthesize the particular antibody is derived from an immunocompetent cell (usually a spleen cell) taken from an immunized donor animal, whereas the ability to continuously divide in cell culture is contributed by the other fusion partner, a tumor cell line (often a myeloma). Early fusions were complicated by the fact that myeloma cell line also produced a monoclonal antibody; thus the hybrid often produced two types of monoclonal antibody, one of myeloma origin and the other directed by the genetic information of the immunocompetent cell. Subsequently, tumor cells lines incapable of producing their own monoclonal have been used, e.g., SP2/0-Ag14 or X63-Ag8.653, thereby simplifying the analysis of the resultant fusion products.

Another technical consideration involves the rationale for selecting the successful fusion events (hybrid cells) from the two types of parental cells. Routinely a million or more cells of each type are used in the fusion protocol, and since fusion does not occur with 100% frequency, the job of trying to recover fusion products from the high background of unfused or self-fused parents can be formidable. As mentioned hybridomas are formed by the fusion of short-lived antibody producing (spleen) cells and long-lived myeloma cells. The desired result is a long-lived cell line which produces antibody. Since the spleen cells have a finite life span in culture one can simply wait an appropriate period for all the nonfused or self-fused spleen cells to die; however one must still recover from the resultant population the long-lived antibody producing cells from the long-lived antibody non-producing cells. A popular means for selection hybrid cells is the so-called HAT-selection system. This system involves the use of the enzyme hypoxanthine-guanine-phosphoribosyl transferase (HGPRT). This enzyme functions in the purine salvage pathway in mammalian cells. These cells are also capable of synthesizing purines de novo. Under most conditions, both pathways probably operate to a certain extent. If a cell lacks HGPRT, the salvage pathway is blocked and purines must be manufactured from non-purine materials.

The chemical 8-azaguanine is an antimetabolite which is capable of masquerading as the purine guanine and replacing it in some of its normal reactions. Azaguanine is incorporated into DNA, interfering with the normal growth pattern and leading to cell death. Since azaguanine must be salvaged, any cell which lacks HGPRT activity cannot utilize azaguanine and will grow in its presence.

A selective system which operates on the same enzyme but in the opposite sense in that HGPRT positive cells are selected is described by J. W. Littlefield (*Science,* 145: 709 (1964)). It is called HAT and contains hypoxanthine, aminopterin and thymidine (HAT medium). Aminopterin is an antimetabolite that prevents de novo purine synthesis and methylation of deoxyuridylate to form thymidylate. Hypoxanthine can serve as a salvagable purine in the event that aminopterin blocks de novo purine biosynthesis while thymidine bypasses the necessity for the methylation of thymidylate. Thus, in the presence of aminopterin, any cell with positive HGPRT activity will proliferate while cells with negative HGPRT activity will die.

In the hybrid system used for selection in accordance with this invention, the myeloma cells are resistant to azaguanine and susceptible to aminopterin, that is, they are HGPRT negative. Thus, they will die in the presence of aminopterin. The antibody producing cells are HGPRT positive. By fusing the cells and growing them in HAT medium without azaguanine (HT medium), the successfully fused cells are selected because the myeloma cells which constitute the proliferating line can only grow where HGPRT activity is present and this activity must be supplied by the HGPRT positive cell line. The antibody producing HGPRT positive cell line are not killed in this medium. They will live for a time but will not proliferate.

Thus, by fusing the cells in a HAT medium, systems are produced in which the myeloma cells and antibody producing cells can grow long enough to produce hybrid cells but in which only the hybrid cells can survive and proliferate. After selection each hybridoma clone is then screened for the ability to produce the particular antibody of interest.

The hybridoma/monoclonal antibody technology has been tremendously successful, one indication being the dedication of nine entire sub-classes within United States Patent Tradem rrk Offices classification system to this technology (935/100 et seq.). Illustrative of the activity is the field of monoclonal antibody technology are U.S. Pat. No. 4,196,265 relating methods of producing monoclonal antibodies to viruses; U.S. Pat. No. 4,404,279 relating to methods of culturing hybridomas and increasing hybridization and U.S. Pat. No. 4,427,653 relating to a method of making monoclonal antibodies in which the antigen preparation is pre-absorbed with certain monoclonal antibodies prior to immunization. Although by no means an exhaustive list, monoclonal antibodies have been developed to the following antigens: *Treponema pallidum* (EPO-83302898.8), hepatitis antigens (EPO-83103858.3), anti-H-Y. (EPO-83301214.9), lens epithelial cells (83301176.0), carcinoembryonic antigen (PCT-W081101469), urokinase (EPO-83100190.4), herpes (EPO-83400074.7), rat hepatocyte (82306409.2), *Schistosoma mansoni* (PCT-W083/01837), Leishmania (PCT-W083/01785, transferrin receptor glycoprotein (EPO-82305658.5), rheumetoid factor (PCT-W083/01118) cell surface antigens of human renal cancer (EPO-82107355.8) alphainterferon (PCT-W081/02899), T-cell antigen (EPO-81300047.8) human suppressor T-cells (EPO-80304348.8).

With respect to plant diseases, Hsu, H. T, et al. (*ASM News,* 50(3): 99–101 (1984)) list 18 plant virus species to which monoclonal antibodies have been developed; included are carnation etched ring virus, potato leaf roll virus, southern bean mosaic virus, tobacco mosaic virus, tomato ringspot virus, and tulip breaking virus.

Monoclonal antibodies to fungal organisms have been developed primarily as a tol for human disease diagnosis. For example, U.K. Patent Applications GB2138444A and GB2138445A relate to monoclonal antibodies reactive with Candida and Aspergillus, respectively.

Disclosed herein are monoclonal antibodies specifically reactive with members of the fungal family Sclerotiniaceae and methods for their production. The antibody is particularly useful for broad range detection of Sclerotinia infections.

BRIEF DESCRIPTION OF THE INVENTION

This invention relates to a hybridoma which produces a monoclonal antibody to an antigen from at least one strain of Sclerotinia.

In a further embodiment the invention provides a monoclonal antibody to an antigen of at least one strain of Sclerotinia.

In a further embodiment the ineention provides a method for preparing hybridomas capable of producing monoclonal antibody to an antigen of a fungus belonging to the genus Sclerotinia comprising:

providing a crude extract of Sclerotinia antigen; immunizing an animal with said extract;

recovering immunocompetent cells from said animal;

fusing said immunocompetent cells with myeloma cells to form hybridomas;

detecting those hybridomas capable of producing monoclonal antibodies to Sclerotinia antigens by affixing the antigen to be detected to a solid support by means of glutaraldehyde cross-linking;

and indicating the presence of monoclonal antibody complexed with said affixed antigen by means of an avidin-biotin enzyme-linked immunoassay.

In a further embodiment the invention provides a method for detecting the presence of Sclerotinia antigen in a sample containing same comprising:

forming a binary complex between said antigen and a first antibody capable of reacting with said antigen;

forming a tertiary complex by contacting the binary complex with a second monoclonal antibody;

detecting the presence of said tertiary complex by contacting the tertiary complex with an analytically detectable immunological reagent, thereby detecting the presence of said Sclerotinia antigen.

In a final embodiment the invention provides a kit for the immunological diagnosis of Sclerotinia infection of plants comprising a carrier being compartmented to receive in close confinement therein:

an antigen extraction means;

a solid support having affixed thereto a antibody capable of forming a binary complex with Sclerotinia antigen; and a binary complex detecting means.

DETAILED DESCRIPTION OF THE INVENTION

This invention relates to methods for the production of monoclonal antibodies to Sclerotinia homoeocarpa, the monoclonal antibodies per se, the hybridoma cell line capable of producing said antibodies and methods and kits employing the monoclonal antibodies to diagnose Sclerotinia infection in plant tissue.

Method of Extraction of Fungal Proteins

Fungi were cultured in 50 ml of PDB (Potato Dextrose Broth) medium in 250 ml flasks, (2 liters of Sclerotinaa homoeocarpa Fitz. were generally employed). After one week the fungal cultures were harvested from the medium, washed twice in PBS (Phosphate buffered saline; pH 7.4). Fungal cultures were transferred into a 300 ml batch chamber of a DYNO-MIll type KDL containing 240 ml of 0.50 mm/lead-free glass beads [IMPANDEX]. Cooling jacket of the Batch chamber was pre-cooled to 8° C. with cold tap water. Extract was ground at 3000 RMP for 5 minutes after which the contents of the batch chamber were transferred to 50 ml polystyrene tubes and centrifuged at 17,000 RPM (34,540 g) in a Sorvall RC-5B refrigerated centrifuge using a size SS-34 rotor. The fungal supernatant was aliquoted and frozen until use. Total protein content of samples were in the range of 0.5–2 mg/ml.

Monoclonal Antibody Production

The procedure is a modification of that developed by Kohler and Milstein (*Nature,* 256: 495 (1975) and Hammerling (*Eur. J. Immunol.,* 7: 743 (1977)).

INJECTIONS: The test animals were 4–5 weeks old female

BALB/c mice purchased from CHARLES RIVER BREEDING

LABORATORIES, INC., Wilmington, Mass.

Day 1

1st injection: 0.05 mg of fungal protein in 0.1 ml of PBS buffer plus 0.1 ml Freund's complete adjuvant. IP injection Day 22

2nd injection: same as above

Day 36

3rd injection: 0.025 mg fungal protein in 0.05 ml solution in 0.05 ml Freund's complete adjuvant. IP injection Day 38

Fusion

Spleen isolation

Each animal was sacrificed by cervical dislocation. The spleen was removed and placed in 20 ml of Dulbecco's Modified Eagle's Medium. The spleen was placed on an 80 mesh sterile screen. The spleen was then cut, perfused with DMEM (Dulbecco's Modified Eagle Medium cat no. 320–1965 Gibco Labs.) and then gently massaged with a sterile plunger from a 0 cc disposable plastic syringe. During the entire process of spleen cell extraction, the screen was continually rinsed with DMEM. Contents were pipetted into a 50 ml disposable centrifuge tube and spun down at 1200 RPM for 10 minutes (centrifugation done at room temperature). The supernatant was decanted and the cell pellet washed with 10 mls of red blood cell lysing solution (0.83% $NH_4Cl$; 0.01M $KHC0_3$; 0.1mM EDTA) for 90 seconds at room temperature. The lysing reaction was stopped by diluting with 40 mls of DMEM. The sample was left to stand for 3 minutes, and the supernatant pipetted to 50 ml centrifuge tubes. After centrifugation, the pellet was washed with 50 ml of DMEM and recentrifuged. The final pellet was resuspended with 5 ml of DMEM. A small sample of the spleen cells was retained for counting and to check for cell viability. Optimal concentration of spleen cells is 10 to the 7 cells per ml.

Myeloma cells (SP2-0-Ag 14) obtained from American Type Culture Collection) were transferred (concentration $1 \times 10^6$ cells per ml) from culture into a 50 ml Falcon tube. The myeloma cells for fusion were centrifuged (1200 RPM for 10 minutes at room temperature). After centrifugation, the supernatant was discarded into a clean glass beaker, the cells were washed with DMEM, and recentrifuged. The spleen cells were added to the tube containing the washed myeloma pellet. The myeloma and speen cells were gently resuspended with the aid of a 10 ml pipette and automatic pipetter and centrifuged for 10 minutes at 1200 RPM at room temperature. Following centrifugation, the supernatant was decanted.

Fusion

The fusion medium, 50% PEG (polyethylene glycol) 1500 (M.A. Bioproducts Cat. #17-7802) prewarmed to 47° C., was suspended in DMEM. One ml of fusion medium was added dropwise to the tube containing the resuspended myeloma and spleen cells—time thirty seconds. The final 7 minutes of the fusion reaction was to allow the gradual dilution of the PEG with DMEM. At the end of the dilution, the final volume in the tube reached 50 mls. During the entire fusion period, the tube was gently tapped to insure proper mixing of the material. The tube was then centrifuged (1200 RPM for 10 minutes at room temperature) and the supernatat removed. Prewarmed HAT medium (described below) (33 ml) was added to the tube, and the cellular contents were suspended using a 10 ml pipette. The final concentration of spleen cells was $1.4 \times 10^6$ cells.

Cells were then added to the 60 central wells of a 96 well microtiter plate (Limbro multiwell). To each well was added 150 ul of fused Myeloma/Spleen material. Outer wells of the microtiter plate were then filled with HAT medium. Microtiter plates were placed in a water jacketed 7% $CO_2$ incubator, temperature 37° C.

Cells were refed with HAT medium every 4 days. Visible hybridoma growth began to appear after 7 to 10 days. A number of different hybridoma lines were produced by the foregoing procedure, each of which produces monoclonal antibodies of the IgG class. The preferred hybridoma is designated as SH3LLIBll-G6-D3. The antibody produced by this hybridoma is of the IgG1 subclass.

| HAT Medium Composition | |
|---|---|
| DULBECCO'S MODIFIED EAGLE MEDIUM cat #320-1965 GIBCO LABS | 766 ml |
| L Glutamine (200 mM) 100 × concentration cat #320-5030 GIBCO LABS | 10 ml |
| Pencillin/Streptomycin solution: 10,000 μ/ml cat #P0781 SIGMA | 10 ml 10 mg/ml |
| Aminopterin (50 ×) cat #A-5159 SIGMA | 4 ml |
| Hypoxanthine/Thymidine solution: Thymidine cat #T-9250 SIGMA Hypoxanthine cat #H-9377 SIGMA add 100 ml sterile water and pH to 8.5 with sterile 1 N NaOH | 10 ml 38.8 mg 136.1 mg |
| Fetal Bovine Serum cat #12-10378 HAZLETON DUTCHLAND, INC. | 200 ml |

Screening for Hybridomas

Those hybridomas producing antibodies to fungal pathogens were identified by using prepared *Sclerotinia homoeocarpa* (Eds.) Fitz. fungal material (protein concentration 10 ug/ml in PBS buffer) and material from related species in an avidin/biotin amplified glutaraldehyde ELISA format.

Standard Screening Protocol

This procedure relates to an enhancement procedure for screening hybridomas secreting antibodies to fungal pathogens.

AVIDIN/BIOTIN GLUTARALDEHYDE
ELISA SCREENING
ELISA - GLUTARALDEHYDE Procedure 1. 200 μl of glutaraldehyde buffer was placed into each well (Immulon I plates), incubated for 3 hours at 55° C., cooled to room temperature and the plates washed 3 times with deionized (DI) water.
2. 200 μl of antigen diluted in 0.15M PBS, pH 7.2, was dispensed into each well. One row was left empty for use as the glutaraldehyde control. The mixture was incubated for 24 hours at 4° C., the remaining suspension discarded and washed 3× with PBS.
3. 200 μl of (mono)ethanolamine solution was dispersed into each well, incubated for 20 hours at 4° C., the remaining solution discarded and plate washed 3X with PBS.
4. 200 μl of appropriate sample was placed into each well, incubated for 2 hours at 33° C. with humidity. The remaining solution was discarded and the plate washed 3× with PBS.
5. The supernatants were aspirated and washed 2 times with 200 μl PBS.
6. Biotinylated anti-mouse IgG or IgM; peroxidase conjugated avidin reagent (VECTOR LABORATORIES mouse anti IgG or IgM; ABC reagent)
   10 ml PBS+100 μl normal horse serum+1 drop biotinylated anti-mouse IgG
   10 ml PBS (0.1% tween)
   add 2 drops ABC reagent A
   immediately add 2 drops ABC reagent B, mix and let stand for 30 minutes before using
7. 75 μl/well biotin/anti-mouse solution was added and incubated for 30 minutes at room temperature.
8. The mixture was aspirated and washed 2 times with 200 μl PBS.
9. ABC reagent (see above) was added at 75 μl well incubated 30 minutes at room temperature, then aspirated and washed 5 times with 200 μl PBS/well.
10. The following substrate solution was added at 200 μl/well.
    Citrate Phosphate Buffer
    7.1 g $Na_2HPO_4$ (500 ml)
    9.6 g citric acid (500 ml)
    adjust pH of first solution to 6.0 by adding citric acid
    50 ml buffer
    20 mg Phenylenediamine-HCL 1,2 benzenediamine (OPD)
    Sigma P 3888
    167 μl 3% $H_2O_2$ The mixture was incubated at room temperature for 10 minutes and absorbance read at 405 nm. Table I shows results observed with an ascites reagent produced with a single cell line, SH3LLIBll-G6-D3, diluted 1:500 in 20% Fetal Calf Serum (FCS) in Dulbecco's Modified Eagle's Medium (DMEM).

Required Solutions

1. Glutaraldehyde buffer: 0.1% glutaraldehyde in 0.1M carbonate buffer. The carbonate buffer, pH 9.0, consists of 1.57 g $Na_2CO_3$ and 2.93g $NaHCO_3$ per liter of DI water.
2. PBS-tween: 8.0 NaCl, 0.2g $KH_2PO_4$, 2.9 g, 1.15 g $Na_2HPO_4$ anhydrous, 0.2 g KCl, per liter of DI water, pH 7.4.
3. (Mono)ethanolamine solution: 1 mg/ml solution (1 g/liter of DI water).

TABLE I

Test With SH3LLIB11-G6-D3

| Fungal Cultures | Source | Absorbance | |
|---|---|---|---|
| *Sclerotinia homoeocarpa* | | | |
| SH-1 | Cole; Penn State | 1.05 | 3+ |
| SH-2 | Cole; Penn State | 0.47 | 2+ |
| SH-3 | Cole; Penn State | 0.55 | 2+ |
| SH-4 | Wilkinson; Illinois | 0.18 | 1+ |
| SH-5 | Gail Worf; Madison, WI | 0.29 | 2+ |
| SH-6 | Gail Worf; Madison, WI | 0.10 | +/− |
| SH-7 | Gail Worf; Madison, WI | 0.43 | 2+ |
| SH-8 | Scotts; Marysville, OH | 0.68 | 2+ |
| *Sclerotinia trifoliorum* | | | |
| ST-1 | ATCC #34326 | 0.04 | − |
| *Sclerotinia minor* | | | |
| SM-2 | ATCC #44236 | 0.03 | − |
| *Sclerotinia sclerotiorum* | | | |
| SS-1 | Nelson; N. Dakota State | 0.04 | − |
| SS-2 | Nelson; N. Dakota State | 0.04 | − |
| SS-3 | Nelson; N. Dakota State | 0.04 | − |
| SS-4 | Nelson; N. Dakota State | 0.04 | − |
| SS-6 | Maxwell; U. of Wisconsin | 0.06 | − |
| *Whetzelinia* (Sclerotinia) *sclerotiorum* | | | |
| SS-7 | Miller; Rancocas, NJ | 0.03 | − |
| *Rhizoctonia solani* | | | |
| RS-1 | Lucas; North Carolina | 0.04 | − |
| RS-2 | Cole; Penn State | 0.07 | − |
| RS-3 | Cole; Penn State | 0.05 | − |
| RS-5 | Lucas; North Carolina | 0.05 | − |
| RS-6 | Larsen; Minnesota | 0.06 | − |
| RS-7 | O'Neil; Beltsville, MD | 0.05 | − |
| RS-8 | Burpee; U. Guelph, Canada | 0.06 | − |
| RS-10 | Burpee; U. Guelph, Canada | 0.08 | − |
| RS-11 | Burpee; U. Guelph, Canada | 0.05 | − |
| RS-12 | Burpee; U. Guelph, Canada | 0.05 | − |
| RS-13 | Burpee; U. Guelph, Canada | 0.09 | − |

TABLE I-continued

| | Test With SH3LLIB11-G6-D3 | |
|---|---|---|
| Fungal Cultures | Source | Absorbance |
| RS-14 | Burpee; U. Guelph, Canada | 0.08 — |
| RS-15 | Burpee; U. Guelph, Canada | 0.08 — |
| *Pythium aphanidermata* | | |
| PA-1 | Larsen; Schmitthener-Wooster, OH | 0.07 — | adjusted protein concentration 10 μg/100 μl

Second Screening Procedure

In addition to the standard screening procedure described above, a second screening was performed utilizing infected material. Specifically, a multiwell ELISA test for detection of dollarspot, *Sclerotinia homoeocarpa*, was performed on infected turfgrass. The test compares results observed with both ascites and supernatants of the following cell lines: SH3LLIB11-G6-D3 and SH3LLIB11-G6-B7.

The turfgrass sample extraction buffer used in the following procedure incorporates a mechanism for the selective deactivation of native turfgrass peroxidase enzyme, thus making it possible to use a conjugate system employing peroxidase.

The following components were employed in the screening procedure:

1. A 96 well plate (immulon I) precoated with glutaraldehyde as described in the first screening.
2. Extraction buffer: Phosphate buffered saline (PBS, pH 7.4) with 5% polyvinylpyrrolidone (mw 14,000) and 3% hydrogen peroxide.
3. Monoclonal antibody: Ascites diluted in 20% FCS in DMEM, 1:500, 1:1000.
4. Conjugate: Biotinylated goat anti-mouse IgG with peroxidase conjugated avidin (ABC Test from Vector Labs).
5. Substrate: 1 mg/ml of urea peroxide in 0.1M sodium citrate, pH 4.5. To each 15 ml of urea peroxide solution is added 6 mg of orthophenyldiamine (OPD).

The following procedure is followed:

1. Glutaraldehyde coated plates are washed 8 times with water.
2. 100 μl of sample extract is placed in the test wells, and the plate is incubated for 2 hours at 37° C.; this is followed by washing the plate 8 times with PBS buffer.
3. 100 μl of the chosen monoclonal reagent is then placed in the test wells, and again incubated for 2 hours at 37° C., and washed 8 times with PBS buffer.
4. 75 μl of biotinylated goat anti-mouse IgG is further added to the wells and incubated for 30 minutes at room temperature, followed by 8 washings with PBS buffer.
5. 75 μl of peroxidase conjugated avidin is then added, and again incubated for 30 minutes at room temperature, followed by 8 washings with PBS buffer.
6. 200 μl of substrate is added to the wells and incubated for 30 minutes at room temperature.
7. Samples are read at 410 nm absorbance; the results are shown in Table II.

TABLE II

| | Absorbance 410 nm (20 minute incubation) | | | | |
|---|---|---|---|---|---|
| | Fylking grass infected with SH-1 | Fylking grass infected with PA-1 | Fylking grass infected with RS-16* | Fylking grass uninfected | Ext. buffer |
| SH3LLIB11-G6-D3 ascites | | | | | |
| dil (1:500) | 0.73 | 0.16 | 0.21 | 0.16 | 0.12 |
| dil (1:1000) | 0.81 | 0.14 | 0.14 | 0.09 | 0.06 |
| SH3LLIB11-G6-B7 ascites | | | | | |
| dil (1:500) | 0.56 | 0.14 | 0.17 | 0.09 | 0.05 |
| dil (1:1000) | 0.46 | 0.11 | 0.14 | 0.09 | 0.07 |
| SH3LLIB11-G6-D3 supernatants | | | | | |
| 100 ul | 0.52 | 0.10 | 0.10 | 0.05 | 0.06 |
| SH3LLIB11-G6-B7 supernatants | | | | | |
| 100 ul | 0.53 | 0.13 | 0.10 | 0.08 | 0.07 | ascites diluted in 20% Fetal Calf Serum in DMEM
*Rhizoctonia solani* Source: Burpee; U. of Guelph, Canada.

Subcloning Procedure

Those wells giving positive responses to the ELISA tests undergo a limiting dilution so that pure strains of hybridoma cells might be grown. The limiting dilution method involved culturing serially diluted suspensions of hybridomas. Each dilution series was set up in 6–12 wells of a 96 well culture plate. These wells were then retested for specific antibody activity to fungal proteins. Positive wells were then transferred to 20 ml culture flasks for mass culturing.

Deposit of Strains Useful in Practicing the Invention

A deposit of biologically pure cultures of the following hybridomas were made with the American Type Culture Collection, 12301 Parklawn Drive, Rockville, Md. on Nov. 14, 1985. The accession number indicated was assigned after successful viability testing, and the requisite fees were paid. Access to said culture will be available during pendency of the patent application to one determined by the Commissioner to be entitled thereto under 37 C.F.R. §1.14 and 35 U.S.C. §122. All restriction on availability of said culture to the public will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture(s) of the same taxonomic description.

| Hybridoma | ATCC No. |
|---|---|
| Balbc/SP2 SH3LLIB11-G6-D3 | 8944 |

Detection of FungalPathogens and Kits Therefor

This invention contemplates the use of the monoclonal antibodies described above in a system for detection of Sclerotinia infection. Accordingly, a sample of plant material suspected of harboring the organism is subjected to an extraction procedure whereby the plant material is physically disrupted such as by grinding and the resultant crude extract is diluted into water or buffer. A sample of the crude extract is contacted with a first antibody specifically reactive with an antigenic determinant of the organism to be detected. Preferably the antibody is immobilized on a solid support such as the walls of a microtiter plate. The antibody may be a monoclonal antibody or a component of polyclonal sera. After removing the unreacted material by washing, the resulting binary complex (antigen-antibody complex) is contacted with a monoclonal antibody specifically reactive to the antigen to be detected. Of course if a monoclonal is employed as the first antibody the second monoclonal should be reactive with a different antigenic determinant than the first monoclonal, unless it can be shown that the determinant is present in multiple copies in the antigen. By contacting the immobilized binary complex with the second monoclonal antibody, a tertiary complex is formed. After washing to remove any of second antibody which did not bind to the binary complex, the tertiary complex may be detected by a variety of analytical techniques. The second monoclonal could be labelled directly and the tertiary complex indicated. Alternatively, the ELISA system described above may be employed whereby the tertrary complex is reacted with an biotin-labelled, antiimmunoglobulin and that reaction product is subsequently contacted with an avidin-enzyme reagent. Once reacted, the substrate of the enzyme is added and the enzyme reaction product detected, thus indicating the presence of the organism or antigen therefrom.

To facilitate the detection the various reactants are provided in the form of a kit.

What is claimed is:

1. A monoclonal antibody capable of specifically binding with an antigen from *Sclerotinia homoeocarpa*.

2. The antibody of claim 1 wherein the antibody is of the IgG class.

3. A hybridoma which produces a monoclonal antibody which is capable of specifically binding with an antigen from *Sclerotinia homoeocarpa*.

4. The hydridoma of claim 3 wherein said monoclonal antibody is of the IgG class.

5. The hybridoma of claim 4 wherein said monoclonal antibody is of the IgG1 class.

6. The hybridoma of claim 5 having all of the identifying characteristics of ATCC HB 8944.

7. A monoclonal antibody produced by culturing the hybridoma of claim 3.

8. A monoclonal antibody produced by culturing the hybridoma of claim 4.

9. A monoclonal antibody produced by culturing the hybridoma of claim 5.

10. A monoclonal antibody produced by the hybridoma of claim 6.

11. The monoclonal antibody of claim 10 wherein said antibody is labelled with an analytically detectable reagent.

12. The monoclonal antibody of claim 11 wherein said reagent is selected from the group consisting of biotin, a fluorensent dye, a radioactive material and an enzyme.

13. The monoclonal antibody of claim 10 wherein said antibody is immobilized onto a solid support.

14. A method or detecting the presence of an antigen from *Sclerotinia homoeocarpa* in a sample containing the antigen comprising:
    forming a binary complex between said antigen and a first antibody capable of reacting with said antigen;
    forming a tertiary complex by contacting the binary complex with a second monoclonal antibody;
    detecting the presence of said tertiary complex by contacting the tertiary complex with an analytically detectable immunological reagent thereby detecting the presence of the antigen from *Sclerotinia homoeocarpa*.

15. The method according to claim 14 wherein said first antibody is monoclonal or polyclonal.

16. The method according to claim 15 wherein said first antibody is immobilized to a solid support.

17. The method according to claim 24 wherein said analytically detectable immunological reagent is a third antibody reactive to said second monoclonal antibody.

18. The method according to claim 17 wherein said detection is by means of a label selected from the group consisting of biotin, a radioactive material, fluorescent dyes, and an enzyme.

19. The method according to claim 18 wherein the label is biotin and its presence is indicated by reaction with avidin.

20. The method according to claim 19 wherein said avidin is complexed with an enzyme and said complex is detected by measuring of the enzyme reaction product.

21. A kit for the immunological diagnosis of *Sclerotinia homoeocarpa* infection of plants comprising a carrier being compartmented to receive in close confinement therein
    an antigen extraction means;
    a solid support having affixed thereto a monoclonal antibody capable of specifically binding with Sclerotinia antigen; and
    a binary complex detecting mean.

22. The kit according to claim 21 wherein said binary complex detecting means comprises a biotin-avidin enzyme linked immunoassay system.

* * * * *